United States Patent

Preikschat

[11] 4,174,498
[45] Nov. 13, 1979

[54] APPARATUS AND METHOD FOR PROVIDING SEPARATE CONDUCTIVITY, DIELECTRIC COEFFICIENT, AND MOISTURE MEASUREMENTS OF PARTICULATE MATERIAL

[76] Inventor: Fritz K. Preikschat, 16020 Lake Hills Blvd., Bellevue, Wash. 98008

[21] Appl. No.: 891,535

[22] Filed: Mar. 30, 1978

[51] Int. Cl.$^2$ .................................................. G01R 27/00
[52] U.S. Cl. ............................... 324/57 R; 324/61 R; 324/DIG. 1
[58] Field of Search ............... 324/65 R, 61 R, 57 R, 324/DIG. 1

[56] References Cited

U.S. PATENT DOCUMENTS

| | | | |
|---|---|---|---|
| 3,746,975 | 7/1973 | Maltby | 324/61 R X |
| 3,774,237 | 11/1973 | Hardway, Jr. | 324/61 R |
| 3,774,238 | 11/1973 | Hardway, Jr. | 324/61 R |
| 3,778,707 | 12/1973 | Vogel | 324/61 R |
| 3,873,927 | 3/1975 | Overall | 324/61 R X |
| 3,986,110 | 10/1976 | Overall et al. | 324/65 R X |
| 4,135,151 | 1/1979 | Rogers et al. | 324/61 R |

Primary Examiner—Stanley T. Krawczewicz
Attorney, Agent, or Firm—Christensen, O'Connor, Johnson & Kindness

[57] ABSTRACT

A bridge circuit, interconnected with a sample box containing a sample of particulate material, is energized by a test signal and provides a bridge output signal whose phase, relative to the phase of the test signal, and whose amplitude are related to the electrical admittance of the sample. After compensation for variations in temperature and bulk density of the sample, the bridge output signal is applied to a first controlled rectifier which is also provided with a reference signal whose frequency is identical to that of the test signal and whose phase is shifted by a predetermined amount from that of the test signal. The first controlled rectifier passes only that component of the bridge output signal in-phase with the test signal to provide a first DC signal related to the measured conductivity of the sample. The bridge output signal is also applied to a second controlled rectifier which is also provided with the reference signal, as coupled through a 90° phase shift circuit. The second controlled rectifier passes only that component of the bridge output signal which is 90° out-of-phase with that of the test signal to provide a second DC signal related to the measured dielectric coefficient of the sample. In order to obtain a signal which is related to the moisture content of the sample, the first DC signal is applied to one input of a differential amplifier whose other input is provided with a threshold signal representing a predetermined conductivity value. When the measured conductivity exceeds the predetermined value, the differential amplifier provides an output signal equal to the difference between the measured conductivity and the predetermined value. This output signal is modified by a signal shaper into a signal representing a corresponding percentage. A multiplier circuit multiplies the second DC signal by the percentage represented by the output signal from the signal shaper to obtain a moisture correction signal which is subtracted from the second DC signal to obtain an output signal related to measured moisture content. An alarm indication is also provided when the measured conductivity goes above a value representing an excess conductivity condition in the sample.

22 Claims, 2 Drawing Figures

APPARATUS AND METHOD FOR PROVIDING SEPARATE CONDUCTIVITY, DIELECTRIC COEFFICIENT, AND MOISTURE MEASUREMENTS OF PARTICULATE MATERIAL

FIELD OF THE INVENTION

This invention generally relates to electrical impedance measuring apparatus, and more particularly, to such apparatus useful in determining the electrical impedance of various particulate materials such as wood chips.

BACKGROUND OF THE INVENTION

Apparatus is known to the prior art for measuring the electrical impedance of particulate materials, such as wood chips, grain, hogged fuel, sawdust, coal, and various ore concentrates. In the particular case of wood chips, such apparatus may include a sample box for receiving and retaining a sample of wood chips during measurement, the sample box defining a pair of electrodes which form part of an electrical bridge circuit which is energized by a high frequency, alternating current signal. The bridge circuit provides an output signal which is related to the electrical impedance of the wood chips contained within the sample box. After compensation for temperature and bulk density variations of the wood chips, the bridge output signal is then rectified in a controllable manner to provide a DC output signal which is related to a selected component, either resistive or reactive, of the measured electrical impedance.

Illustrative examples of such impedance measuring apparatus can be found in U.S. Pat. No. 3,781,671, issued Dec. 25, 1973 to Fritz K. Preikschat, and entitled IMPEDANCE MEASURING BRIDGE CIRCUIT; U.S. Pat. No. 3,824,461, issued July 16, 1974 to Fritz K. Preikschat, and entitled ELECTRICAL IMPEDANCE MEASURING APPARATUS; and U.S. Pat. No. 3,992,665, issued Nov. 16, 1976 to Fritz K. Preikschat and entitled ELECTRICAL IMPEDANCE MEASURING APPARATUS. Each of the foregoing patents is expressly incorporated by reference herein.

It is particularly desirable to accurately measure the moisture content of wood chips, since that moisture content is an important factor in determining the liquor-wood ratio used in processes for making pulp from wood chips. Heretofore, it has been recognized that the dielectric coefficient of wood chips is directly related to moisture content. Therefore, the electrical impedance measuring apparatus of the prior art has been operative to measure the reactive component of the measured electrical impedance, and to thereby provide an output signal which is related to the measured dielectric coefficient of the wood chips.

It has become increasingly evident, however, that the measured dielectric coefficient is not in all cases a true measure of the moisture content of wood chips. The reasons for this lack of correlation between measured dielectric coefficient and moisture content can usually be traced to variations in the physical characteristics of the wood chips. The prior art, as typified by the aforementioned patents, recognizes that both temperature and bulk density variations in the wood chips can affect the dielectric coefficient measurement, and therefore provide means to compensate for such variations. The present invention is based on the recognition that there are certain other factors that also affect the dielectric coefficient measurement and which must be taken into account in order to obtain an accurate measurement of moisture content.

For example, a sample of wood chips typically includes a varying percentage, by weight, of what are termed "fines," or, wood particles such as sawdust which have an average size less than ¼ inch screen mesh. FIG. 1 represents a typical plot of the variation in measured dielectric coefficient, which in turn is related to the reactive component of the measured electrical impedance, and the variation in measured conductivity, which in turn is related to the resistive component of the measured electrical impedance, with variation in the percentage of fines by total weight in a sample of chips. It will be seen that both the measured dielectric coefficient and the measured conductivity increase with an increase in the percentage of fines, and that an increase in the percentage of fines of approximately 10% results in an increase in measured conductivity of approximately 50% and an increase in measured dielectric coefficient of approximately 5%. It has been postulated that the increase in measured conductivity is due to a more effective surface-to-surface contact between the individual chips provided by the increased amount of fines, and that the increase in measured dielectric coefficient is related to the increase in conductivity, inasmuch as the measured dielectric coefficient is that of an equivalent circuit including the actual dielectric coefficient of the wood chips in parallel with the actual conductivity between wood chips.

As yet another example, the logs used to produce wood chips are in many cases stored in salt water whose ionic conductivity may vary. As a result, the conductivity of a sample of wood chips may also vary so that the measured dielectric coefficient is not truly representative of the moisture content of the wood chips.

As yet another example, when wood chips are held in storage, they are subject to decomposition largely caused by fungi attack, which through the action of enzymes, causes a breakdown in the cellulosic components of the chips. If the temperature of the chips exceeds 70–75° C., an additional deterioration occurs through oxidation and respiration effects. As a result, acetic acid is formed which increases the conductivity of the chips to similarly increase the measured dielectric coefficient.

It is therefore an object of this invention to provide an electrical impedance measuring apparatus which is capable of more accurately determining the moisture content of particulate materials than the electrical impedance measuring apparatus of the prior art.

In pulping processes, it is often important to know when wood chips being processed have an unusually high percentage of fines, or contain an unusually high percentage of salt water, or are significantly degraded. For example, the fines in wood chips will absorb the active alkali in a cooking liquor typically used in a pulping process more quickly than the large wood chips, thereby reducing the effective alkali concentration earlier in the process, with the result that increased amounts of alkali must be added to the liquor to obtain a uniform pulp. As another example, degradation of wood chips results in a higher than normal proportion of chemical components that are active in the alkali which causes an excessive liquor consumption and reduction in yield. Also, the acetic acid produced as a result of chip decomposition requires increased amounts of alkali in the liquor. Since conductivity is a measure of the fines content and the amount of degradation of a given sample of wood chips, it is desirable to measure conductivity directly to provide information that can be used in the control of a pulping process in order to obtain a more uniform pulp product.

It is therefore a further object of this invention to provide an electrical impedance measuring apparatus which is capable of providing separate measurements of both the conductivity and dielectric coefficient of particulate material.

SUMMARY OF THE INVENTION

Briefly, these objects, and others that will be realized from a consideration of the following portion of the specification, are achieved by the use of a method for obtaining an accurate measurement of the moisture content of particulate material. The method comprises the steps of obtaining a measurement of the conductivity of the particulate material, obtaining a measurement of the dielectric coefficient of the particulate material, and varying the measurement of dielectric coefficient in a predetermined relationship with the measurement of conductivity to obtain a measurement of moisture content.

In its preferable form, the measurement of dielectric coefficient is decreased only in response to proportionate increases in the measurement of conductivity. In most situations, the measurement of dielectric coefficient is decreased only in response to proportionate increases in the measurement of the conductivity above a predetermined threshold value, below which value variations in conductivity have no appreciable effect on the measured moisture content of the particulate material.

The apparatus of the present invention includes a sample box, a signal generator, and a bridge circuit constructed substantially as shown and described in the aforementioned U.S. Pat. No. 3,781,671, 3,824,461, and 3,992,664, but modified to provide separate signals respectively related to the measured conductivity and to the measured dielectric coefficient of a sample of particulate material contained within the sample box and further including a means responsive to the measured conductivity and measured dielectric coefficient signals to obtain a moisture content signal by the use of a method similar to that previously described.

In the particular case where the particulate material comprises wood chips, the threshold value below which no change in the dielectric coefficient signal is made is substantially 2000 micromhos. For every 2000 micromho increase in the measured conductivity above this threshold value, the measured dielectric coefficient is linearly decreased by 5%.

BRIEF DESCRIPTION OF THE DRAWINGS

The invention can best be understood by reference to the specification, taken in conjunction with the accompanying drawings in which.

DESCRIPTION OF THE PREFERRED EMBODIMENT

Figure 1:
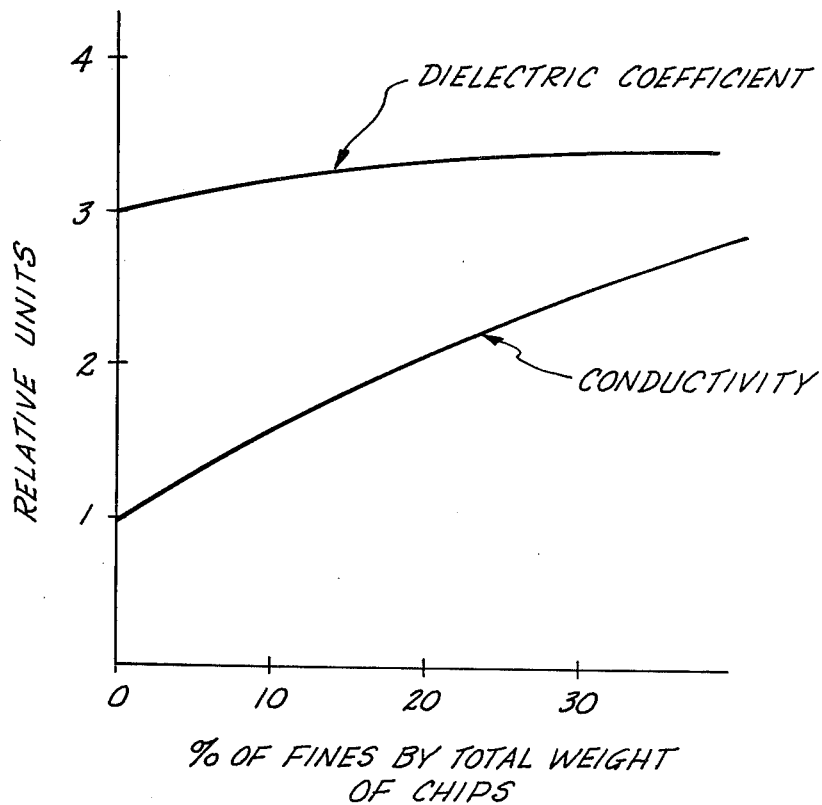
FIG. 1 is a graph showing the relationship between dielectric coefficient and conductivity with variation in fines content of a sample of wood chips, as previously described.
Figure 2:
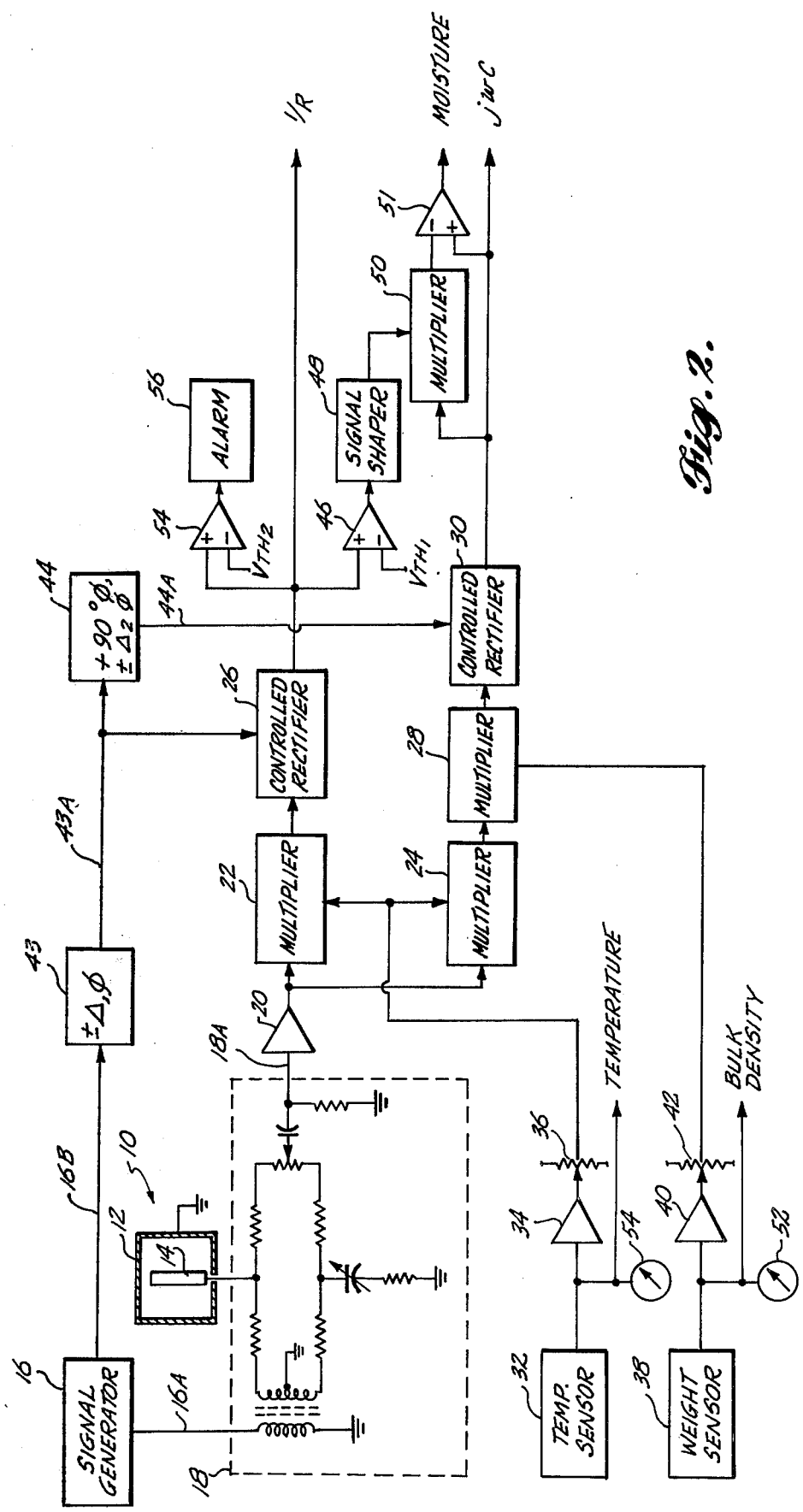
FIG. 2 is a block diagram of the preferred embodiment of the present invention.

With reference now to FIG. 2, a sample box 10, which may be of a type more completely described in the aforementioned U.S. Pat. No. 3,781,671, 3,824,461 and 3,992,665, is shown in plan view and includes a grounded electrode portion 12 which is shaped as a box having a substantially rectangular cross-section. An active center electrode 14, comprising a metallic plate, is disposed in the interior of the sample box defined by grounded electrode portion 12 and in parallel, spaced relationship to the side walls thereof so that a uniform electrical field may be created within the sample box 10. The sample box 10 has an inlet and an outlet, not illustrated, which together with the grounded electrode portion 12 and the active center electrode 14 define a constant volume within the sample box 10 into which a predetermined sample of particulate material is placed and retained for measurement.

A signal generator 16 provides a stabilized test signal, of a certain frequency and phase, on a lead 16A to a bridge circuit 18 of a type whose structure and operation is described in more detail in the aforementioned U.S. Pat. No. 3,781,671, 2,824,461 and 3,992,665. As can be seen, the bridge circuit 18 is interconnected with the active center electrode 14 of the sample box 10, and with ground potential. In operation, the bridge circuit 18 provides a high frequency signal to electrode 14 which creates a high frequency electrical field in the interior of the sample box 10 and therefore in the sampled material contained therein. The sampled material causes an imbalance in the bridge circuit 18 so that an output signal is provided on load 18A thereof whose phase, relative to the phase of the test signal on lead 16A from signal generator 16, and amplitude are related to the electrical admittance, or reciprocal impedance, of the sampled material.

The output signal from bridge circuit 18 on lead 18A is amplified in an amplifier 20 and coupled to the inputs of multipliers 22, 24. The output of multiplier 22 is connected to the input of a controlled rectifier 26 upon whose output appears a DC signal, to be described hereinafter, which is proportional to the measured conductivity (1/R) of the sampled material. The output of multiplier 24 is connected to the input of a multiplier 28 whose output is connected to the input of a controlled rectifier 30 upon whose output appears a DC signal, to be described hereinafter, which is proportional to the measured dielectric coefficient ($j\omega C$) of the sampled material.

Both the measured conductivity and the measured dielectric coefficient are subject to variation, depending upon the temperature of the sampled material. Accordingly, a temperature sensor 32 is provided which is preferably mounted in proximity to the sample box 10 to provide an output signal which is related to the average measured temperature of the sampled material. The output signal from temperature sensor 32 is amplified in an amplifier 34 and has its level adjusted by a potentiometer 36 to develop a temperature correction signal which is supplied to control inputs of multipliers 22 and 24. Multipliers 22 and 24 operate to multiply the value of the output signal from the bridge circuit 18, as amplified by the amplifier 20, by the temperature correction signal to obtain respective output signals which are compensated for temperature variations in the sampled material. The amount of temperature compensation is determined by the gain factor of amplifier 34 and by the setting of potentiometer 36, and the multipliers 22 and 24 may each comprise a variable gain amplifier whose gain is adjusted in relation to the level of the temperature correction signal supplied thereto.

The measured dielectric coefficient is also subject to variation, depending on the bulk density of the sampled material. Accordingly, a weight sensor 38 is provided which, in its preferred form, may comprise a load cell which is mounted so as to provide an output signal related to the weight of the sampled material within the sample box 10. Since the sample box 10 has a constant volume, the output signal from weight sensor 38 is also related to bulk density. The output signal from weight sensor 38 is amplified by an amplifier 40 and has its level adjusted by a potentiometer 42 to develop a bulk density correction signal which is supplied to a control input of multiplier 28. Multiplier 28 functions to multiply the value of the output signal from the bridge circuit 18, as amplified by the amplifier 20, and as compensated by the multiplier 24 by the bulk density correction signal to obtain an output signal which is compensated for bulk density variations in the sampled material. The amount of bulk density compensation is determined by the gain factor of amplifier 40 and by the settting of potentiometer 42, and the multiplier 28 may comprise a variable gain amplifier whose gain is adjusted in relation to the level of the bulk density correction signal supplied thereto.

Signal generator 16 also provides a signal on a lead 16B which has a frequency equal to that of the test signal supplied on lead 16A to bridge circuit 18 and whose phase is carefully controlled so as to be in phase with that test signal. The signal on lead 16B is applied to a phase shift circuit 43 which provides, on its output 43A, a reference signal whose frequency is identical to that of the test signal and whose phase is shifted by a predetermined amount $\Delta_1\phi$ from that of the test signal to compensate for phase shifts in the bridge output signal occurring in the portion of the apparatus from bridge output 18A to the input of controlled rectifier 26. The reference signal on output 43A is applied to controlled rectifier 26 which accordingly operates to pass only that component of the output signal from the bridge circuit 18 that is in phase with the test signal. Controlled rectifier 26 also includes a filter circuit, not illustrated, for converting the thus-passed component of the output signal from bridge circuit 18 into a corresponding DC signal. Since the in-phase component of the output signal from the bridge circuit 18 is the conductance component of that signal, the DC signal from controlled rectifier 26 is therefore proportional to the measured conductivity (1/R) of the sampled material.

The reference signal on output 43A is also applied to the input of a phase shift circuit 44 which provides a second reference signal on its output 44A to controlled rectifier 30 whose frequency is the same as the test signal appearing on lead 16A. The phase of the second reference signal on output 44A is carefully controlled to be advanced 90° from that of the reference signal on output 43A, plus or minus a predetermined amount $\Delta_2\phi$ to compensate for phase shifts in the bridge output signal occurring in the portion of the apparatus from bridge output 18A to the input of controlled rectifier 30. Controlled rectifier 30 accordingly functions to pass only that component of the output signal from bridge circuit 18 that leads the test signal by 90°. Controlled rectifier 30 also includes a filter circuit, not illustrated, for converting the thus-passed component of the electrical output signal from bridge circuit 18 into a corresponding DC signal. Since the 90° out-of-phase component of the output signal from the bridge circuit 18 is the susceptance (or reciprocal reactance) component of that signal, it will be appreciated that the DC signal from controlled rectifier 30 is proportional to the measured dielectric coefficient ($j\omega C$) of the sampled material.

As previously described, the measured dielectric coefficient of a particulate material, such as wood chip, increases with increases in measured conductivity so as to not truly reflect the actual moisture content of the particulate material. In order to more accurately determine the moisture content, the DC signal from controlled rectifier 26, or, the measured conductivity signal, is applied to a noninverting input of a differential amplifier 46 whose inverting input is provided with a first threshold voltage $V_{TH1}$. For many particulate materials, there is no appreciable change in the measured dielectric coefficient for variation in measured conductivity below a predetermined threshold value. In the case of wood chips, this predetermined value is approximately 2000 micromhos (a resistance of 500 ohms). Therefore, the level of the first threshold voltage $V_{TH1}$ is set to equal the level of the conductivity signal obtained when the measured conductivity is at such a threshold value, e.g., 2000 mircomhos. As long as the measured conductivity is below the threshold value, differential amplifier 46 provides no output signal. When the measured conductivity goes above the threshold value, differential amplifier 46 provides an output signal proportional to the difference between the level of the measured conductivity signal and that of the first threshold voltage $V_{TH1}$.

The output signal from differential amplifier 46 is coupled through a signal shaper 48 to the control input of a multiplier 50 which is also provided with the measured dielectric coefficient signal. Preferably, signal shaper 48 provides an output signal which is linearly related to the level of the output signal from differential amplifier 46, and therefore to the amount by which the measured conductivity exceeds the threshold value established by $V_{TH1}$. Multiplier 50 functions to multiply the value of the measured dielectric coefficient signal by the value of the output signal from signal shaper 48 to obtain a moisture correction signal which is applied to the inverting input of a differential amplifier 51 whose noninverting input is provided with the measured dielectric coefficient signal. Differential amplifier 51 functions to reduce the level of the measured dielectric coefficient signal in relation to the level of the moisture correction signal from multiplier 50 to produce a signal on its output which is proportional to the measured moisture content of the sampled material.

In the particular case of wood chips, the threshold value established by the first threshold voltage $V_{TH1}$ is 2000 micromhos as previously discussed. It is desirable to linearly decrease the actual level of the measured dielectric coefficient signal by 5% for every increase in the level of the measured conductivity signal above the threshold value representing 20% of a maximum level of the measured conductivity signal. This maximum level represents a measured conductivity of approximately 10,000 micromhos (a resistance of 100 ohms). In this case, the signal shaper 48 may comprise a gain circuit which is adapted to provide an output signal proportional to the level of the output signal from differential amplifier 46. The actual level of the output from signal shaper 48 represents a multiplication factor in the range of 0%-20% and is at its minimum level, or a 0% multiplication factor, when the output from differential amplifier 46 is zero, e.g., the level of the measured conductivity signal repesents a measured conductivity of 2000 micromhos, and which is at its maximum level, or a multiplication factor of 20%, when the output signal from differential amplifier 46 represents a measured conductivity of 8000 micromhos above the threshold value, or, a measured conductivity of 10,000 micromhos.

The moisture correction signal at the output of multiplier 50 therefore ranges between zero and a maximum level representing 20% of the measured dielectric coefficient signal, and is substracted in differential amplifier 51 from the measured dielectric coefficient signal to produce the moisture content signal which is compensated for variations in the conductivity of the sampled material. As can be appreciated, the moisture content signal comprises the measured dielectric coefficient signal which is unchanged for measured conductivities at or below 2000 micromhos, and which is decreased in inverse proportion to increases in conductivity above 2000 micromhos, up to a maximum reduction of 20% for a conductivity of 10,000 micromhos.

The present invention also contemplates that nonlinear relationships be utilized in the correction of the dielectric coefficient signal to obtain an accurate determination of moisture content, in which case the signal shaper 48 may provide an output signal which is logarithmically or exponentially related to the level of the output signal from differential amplifier 46.

The conductivity (1/R), moisture content and dielectric coefficient (jωC) signals from the electrical impedance measuring apparatus may be supplied to appropriate indicators, or to a computer (through corresponding A/D conversion circuits) for data analysis purposes, or to equipment for controlling a pulping process, in which case the conductivity, moisture content and dielectric coefficient signals may be used to control the amount of liquor and/or alkali utilized in the pulping process. If desired, the bulk density signal appearing on the output of weight sensor 38 and the temperature signal appearing on the output of temperature sensor 32 may also be directly indicated (by means of indicators 52 and 54), or supplied to a computer or control circuit for data analysis and control purposes.

In many cases, it is desirable to provide a direct indication of an excess conductivity condition in the sampled material so as to allow an operator, for example, one who is controlling a pulping process, to take appropriate corrective action. In such a case, the measured conductivity signal is applied to the noninverting input of a differential amplifier 54 whose inverting input is supplied with a second threshold voltage $V_{TH2}$. The level of $V_{TH2}$ is chosen to equal the level of the measured conductivity signal representing a conductivity value at which a direct indication is desirable. In the case of wood chips, this conductivity value is approximately 10,000 micromhos. As long as the measured conductivity remains below this value, differential amplifier 54 provides no output. When the measured conductivity exceeds this value, differential amplifier 54 provides an output signal which is coupled to an alarm 56, or other suitable indicator, for immediately indicating an excess conductivity condition.

While the invention has been described with reference to a preferred embodiment, it is to be clearly understood by those skilled in the art that the invention is not limited thereto, and that the scope of the invention is to be interpreted only in accordance with the appended claims.

The embodiments of the invention in which an exclusive property or privilege is claimed are defined as follows:

1. An apparatus for providing a moisture content signal whose value is related to the measured moisture content of particulate material, said apparatus comprising:
    (a) first means for providing a conductivity signal whose value is related to the measured conductivity of said particulate material;
    (b) second means for providing a dielectric coefficient signal whose value is related to the measured dielectric coefficient of said particulate material; and
    (c) third means responsive to said conductivity and said dielectric coefficient signals for varying the value of said dielectric coefficient signal in a predetermined relationship with the value of said conductivity signal to obtain said moisture content signal.

2. An apparatus as recited in claim 1, wherein said third means is adapted to decrease the value of said dielectric coefficient signal in response to proportionate increases in the value of said conductivity signal to obtain said moisture content signal.

3. An apparatus as recited in claim 2, wherein said third means is further adapted to reduce the value of said dielectric coefficient signal only when the value of said conductivity signal exceeds a predetermined threshold value representing a measured conductivity below which variations in conductivity have no appreciable effect on the measured moisture content of said particulate material.

4. An apparatus as recited in claim 3, wherein said third means includes:
    (a) a source of a threshold signal whose value is related to said predetermined threshold value;
    (b) means for providing a first output signal whose value is proportional to the difference between the value of said conductivity signal and the value of said threshold signal when the value of said conductivity signal exceeds that of said threshold signal;
    (c) signal shaping means for providing a second output signal whose value is linearly related to that of said first output signal;
    (d) multiplier means for multiplying the value of said dielectric coefficient signal by that of said second output signal to obtain a moisture correction signal whose value is proportional to the product of the values of said dielectric coefficient signal and said second output signal; and
    (e) means for subtracting the value of said moisture correction signal from that of said dielectric coefficient signal to obtain said moisture content signal.

5. An apparatus as recited in claim 3, wherein said particulate material is wood chips, said predetermined threshold value is substantially 2000 micromhos, and wherein the value of said dielectric coefficient signal is linearly decreased by substantially 5% of every substantially 2000 micromho increase in the value of said conductivity signal above said predetermined threshold value.

6. An apparatus as recited in claim 1, further comprising fourth means for providing an output indication when the value of said conductivity signal exceeds a predetermined threshold value representing an excess conductivity condition in said particulate material.

7. An apparatus as recited in claim 6, wherein said fourth means comprises:
   (a) a source of a threshold signal whose value is related to said predetermined threshold value;
   (b) means for providing an output signal when the value of said conductivity signal exceeds that of said threshold signal; and
   (c) alarm means responsive to said output signal for providing said output indication.

8. An apparatus as recited in claim 6, wherein said particulate material is wood chips, and wherein said predetermined threshold value is substantially 10,000 micromhos.

9. An electrical impedance measuring apparatus for providing separate conductivity, dielectric coefficient, and moisture measurements of a sample of particulate material, said apparatus comprising:
   (a) a sample box for containing a sample of particulate material, said sample box including an outer, grounded electrode portion and an active, center electrode disposed within said outer, grounded electrode portion;
   (b) a signal generator providing a test signal of a predetermined frequency and phase;
   (c) a bridge circuit responsive to said test signal and interconnected with said active, center electrode and ground potential to thereby provide a bridge output signal whose frequency is equal to that of said test signal and whose phase, relative to the phase of said test signal, and whose amplitude are related to the electrical admittance of said sample;
   (d) first means responsive to said bridge output signal for passing only that component of said bridge output signal in phase with said test signal to provide a signal whose value is related to the measured conductivity of said sample;
   (e) second means responsive to said reference signal and to said bridge output signal for passing only that component of said bridge output signal that is 90° out-of-phase with said test signal to provide a signal whose value is related to the measured dielectric coefficient of said sample; and
   (f) third means responsive to said measured conductivity and to said dielectric coefficient output signals for varying the value of said dielectric coefficient signal in a predetermined relationship with the value of said conductivity signal to thereby provide a signal whose value is related to the measured moisture content of said sample.

10. An electrical impedance measuring apparatus as recited in claim 9, further comprising means for compensating said bridge output signal for variation in temperature of said sample.

11. An electrical impedance measuring apparatus as recited in claim 9, further comprising means for compensating said bridge output signal for variation in bulk density of said sample.

12. An electrical impedance measuring apparatus as recited in claim 9, wherein said third means is adapted to decrease the value of said measured dielectric coefficient signal in response to proportionate increases in the value of said measured conductivity signal to obtain said measured moisture content signal.

13. An electrical impedance measuring apparatus as recited in claim 12, wherein said third means is further adapted to reduce the value of said measured dielectric coefficient signal only when the value of said measured conductivity signal exceeds a predetermined threshold value representing a measured conductivity below which variations in conductivity have no appreciable effect on the measured moisture content of said sample.

14. An electrical impedance measuring apparatus as recited in claim 13, wherein said third means includes:
   (a) a source of a threshold signal whose value is related to said predetermined threshold value;
   (b) means for providing a first output signal whose value is proportional to the difference between the value of said measured conductivity signal and the value of said threshold signal when the value of said measured conductivity signal exceeds that of said threshold signal;
   (c) signal shaping means for providing a second output signal whose value is linearly related to that of said first output signal;
   (d) multiplier means for multiplying the value of said measured dielectric coefficient signal by that of said second output signal to obtain a moisture correction signal whose value is proportional to the product of said measured dielectric coefficient signal and said second output signal; and
   (e) means for subtracting the value of said moisture correction signal from that of said measured dielectric coefficient signal to obtain said measured moisture content signal.

15. An electrical impedance measuring apparatus as recited in claim 13, wherein said particulate material is wood chips, said predetermined threshold value is substantially 2000 micromhos, and wherein the value of said measured dielectric coefficient signal is linearly decreased by substantially 5% for every substantially 2000 micromho increase in the value of said measured conductivity signal above said predetermined threshold value.

16. An electrical impedance measuring apparatus as recited in claim 9, further comprising fourth means for providing an output indication when the value of said measured conductivity signal exceeds a predetermined threshold value representing an excess conductivity condition in said sample.

17. An electrical impedance measuring apparatus as recited in claim 16, wherein said fourth means comprises:
   (a) a source of a threshold signal whose value is related to said predetermined threshold value;
   (b) means providing an output signal when the value of said measured conductivity signal exceeds that of said threshold signal; and
   (c) alarm means responsive to said output signal to provide said output indication.

18. An electrical impedance measuring apparatus as recited in claim 16, wherein siad particulate material is wood chips, and wherein predetermined threshold value is substantially 10,000 micromhos.

19. A method for obtaining an accurate measurement of the moisture content of particulate material, said method comprising the steps of:
   (a) obtaining a measurement of the conductivity of said particulate material;

(b) obtaining a measurement of the dielectric coefficient of said particulate material; and
(c) varying said measurement of dielectric coefficient in a predetermined relationship with said measurement of conductivity to obtain a measurement of moisture content.

20. A method as recited in claim 19, wherein said step of varying said measurement of dielectric coefficient comprises decreasing said measurement of dielectric coefficient in response to proportionate increases in said measurement of conductivity.

21. A method as recited in claim 20, further comprising the step of decreasing said measurement of dielectric coefficient only for proportionate increases in said measurement of conductivity above a predetermined conductivity value, below which variations in conductivity have no appreciable effect on said measurement of moisture content.

22. A method as recited in claim 21, wherein said particulate material is wood chips, said predetermined conductivity value is substantially 2000 micromhos, and said measurement of dielectric coefficient is linearly decreased by substantially 5% for every substantially 2000 micromho increase in said measurement of conductivity above said predetermined threshold value.

* * * * *